United States Patent
Cowger et al.

(10) Patent No.: US 9,909,979 B2
(45) Date of Patent: Mar. 6, 2018

(54) SYSTEM AND METHOD FOR DETERMINING A CONCENTRATION OF A COMPOUND IN A SOLVENT

(71) Applicant: Engineered Medical Technologies, Sacramento, CA (US)

(72) Inventors: Bryan John Cowger, Meadow Vista, CA (US); Megan Anzar Babb, Folsom, CA (US); Peichen Chang, Roseville, CA (US)

(73) Assignee: Engineered Medical Technologies, Sacramento, CA (US)

( * ) Notice: Subject to any disclaimer, the term of this patent is extended or adjusted under 35 U.S.C. 154(b) by 91 days.

(21) Appl. No.: 15/046,354

(22) Filed: Feb. 17, 2016

(65) Prior Publication Data

US 2016/0161399 A1    Jun. 9, 2016

Related U.S. Application Data

(63) Continuation-in-part of application No. 14/631,995, filed on Feb. 26, 2015, now Pat. No. 9,291,552.

(60) Provisional application No. 62/091,952, filed on Dec. 15, 2014, provisional application No. 61/995,805, filed on Apr. 22, 2014.

(51) Int. Cl.
| | |
|---|---|
| *G01N 21/00* | (2006.01) |
| *G01N 21/33* | (2006.01) |
| *G01J 1/42* | (2006.01) |
| *G01N 21/03* | (2006.01) |
| *G01N 21/13* | (2006.01) |
| *G01N 21/31* | (2006.01) |
| *G01N 21/17* | (2006.01) |

(52) U.S. Cl.
CPC ........... *G01N 21/33* (2013.01); *G01J 1/42* (2013.01); *G01N 21/03* (2013.01); *G01N 21/13* (2013.01); *G01N 21/31* (2013.01); *G01N 2021/0367* (2013.01); *G01N 2021/1751* (2013.01); *G01N 2201/0446* (2013.01); *G01N 2201/062* (2013.01)

(58) Field of Classification Search
CPC .... G01N 21/534; G01N 21/59; G01N 21/255; G01J 3/42; G01J 1/16
USPC ......................................................... 356/434
See application file for complete search history.

(56) References Cited

U.S. PATENT DOCUMENTS

| | | | |
|---|---|---|---|
| 5,156,952 A | 10/1992 | Litman | |
| 2002/0020206 A1 | 2/2002 | Mason | |
| 2004/0199059 A1 | 10/2004 | Brauker | |
| 2006/0292686 A1* | 12/2006 | Fujikura | G01N 21/253 435/287.2 |
| 2013/0234042 A1* | 9/2013 | Ota | G01N 21/77 250/458.1 |

* cited by examiner

*Primary Examiner* — Tarifur Chowdhury
*Assistant Examiner* — Md M Rahman
(74) *Attorney, Agent, or Firm* — Schwabe, Williamson and Wyatt P.C.

(57) ABSTRACT

The present describes a system and method for determining the concentration of tetrahydrocannabinol (THC) including a tray comprising a first analyte including an infusion of a solvent and cannabis, a light emitting element configured to illuminate the first analyte, a light receiving element configured to receive a first light transmitted through the first analyte, and a control circuit configured to calculate a concentration of tetrahydrocannabinol in the first analyte based at least in part on the first light.

13 Claims, 14 Drawing Sheets

SYSTEM AND METHOD FOR DETERMINING A CONCENTRATION OF A COMPOUND IN A SOLVENT

RELATED APPLICATIONS

The present disclosure is a continuation-in-part of U.S. application Ser. No. 14/631995, filed Feb. 26, 2015, and titled "System and Method for Determining the Concentration of Tetrahydrocannabinol," which claims priority to U.S. provisional application 61/995805, filed Apr. 22, 2014, and titled "Method of Estimating the Concentration of the Chemical Tetrahydrocannabinol (THC) and Other Active Chemicals in Lipids" and to U.S. provisional application 62/091952, filed Dec. 15, 2014, and titled "System and Method for Determining the Concentration of Tetrahydrocannabinol," all of which are incorporated herein by reference in their entirety.

TECHNICAL FIELD

The present disclosure relates to a system and method for determining a concentration of a compound in various solvents including oils and other lipids.

BACKGROUND

Cannabis is often used for its medicinal benefits. The principal psychoactive constituent compound of cannabis is tetrahydrocannabinol (THC), which, when smoked, eaten, ingested, or otherwise consumed, may cause feelings of relaxation and euphoria in some users.

DRAWINGS DESCRIPTION

FIG. 1 is a block diagram of an embodiment of a system for measuring the concentration of THC in an infusion according to the present disclosure;

FIGS. 2A-C are different views of an embodiment of a device for measuring the concentration of THC in an infusion according to the present disclosure;

FIGS. 3A-C are different views of an embodiment of a tray for measuring the concentration of THC in an infusion according to the present disclosure;

Figure 7A:
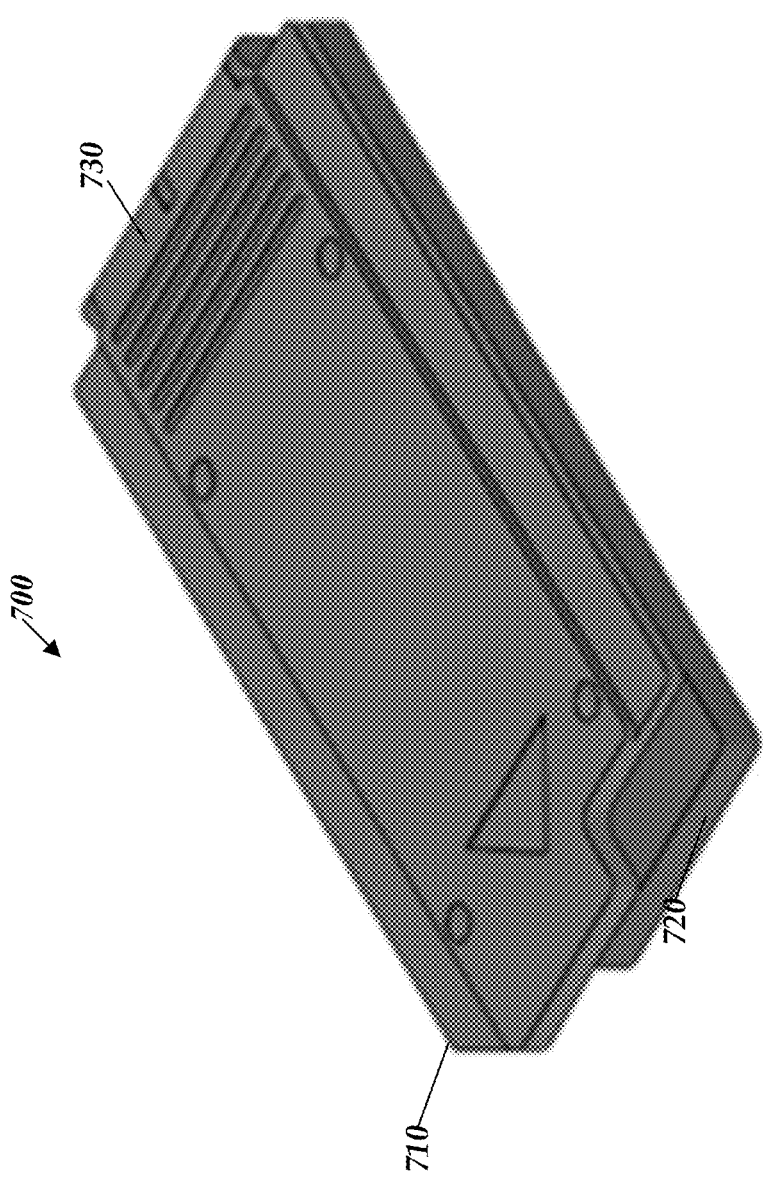
Figure 7B:
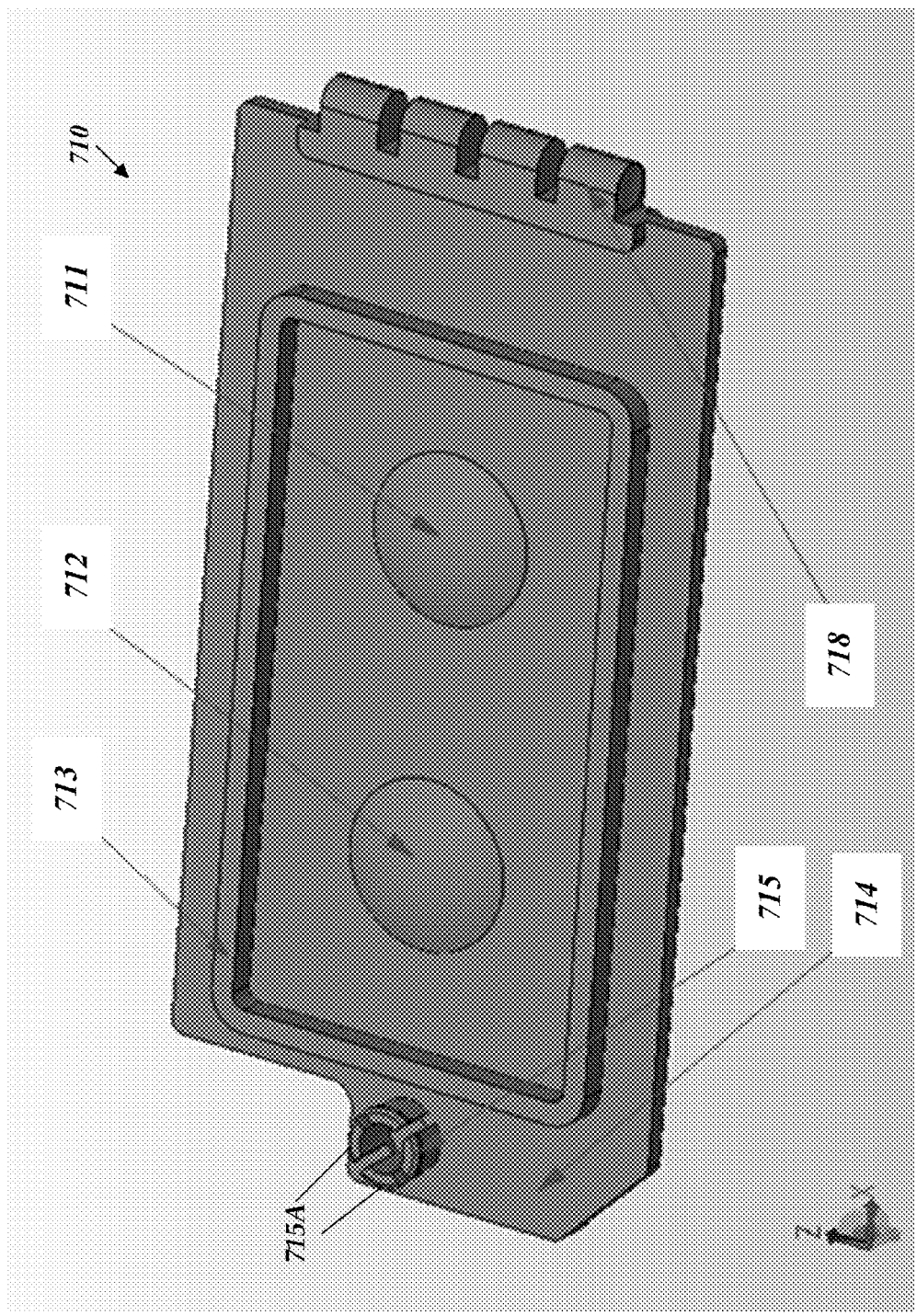
Figure 7C:
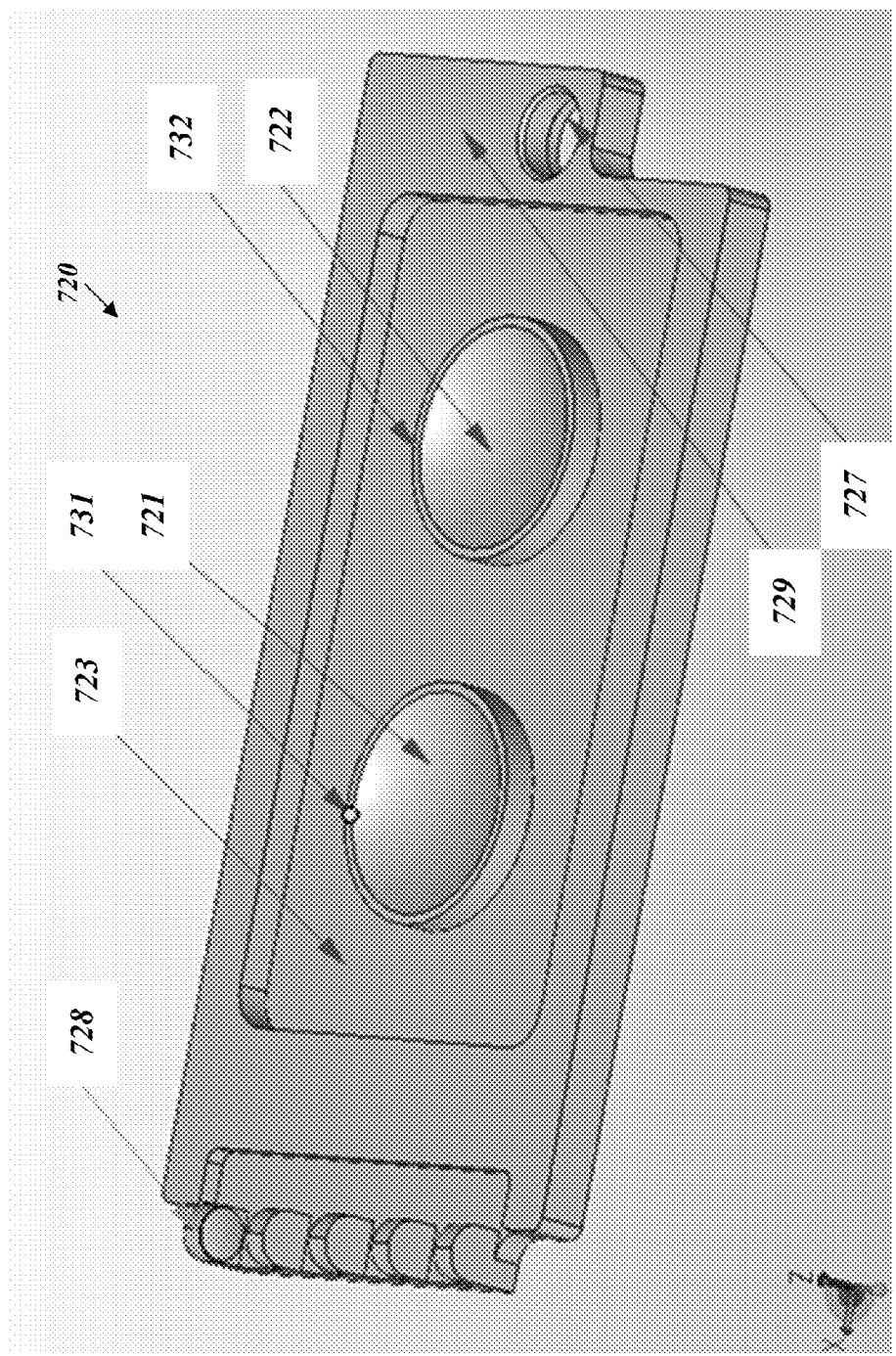
Figure 7D:
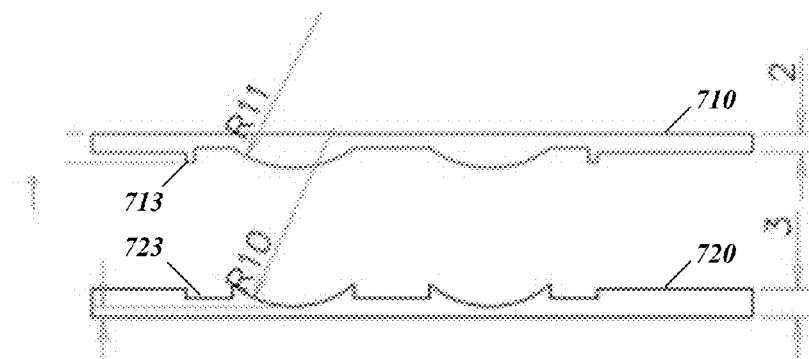
Figure 7E:
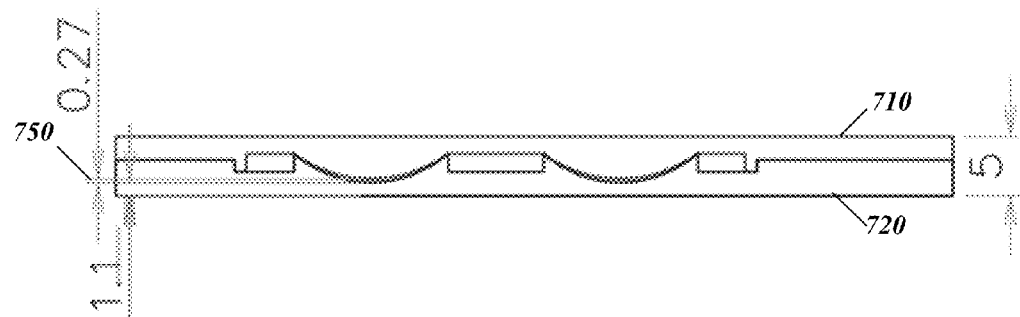
Figure 8:
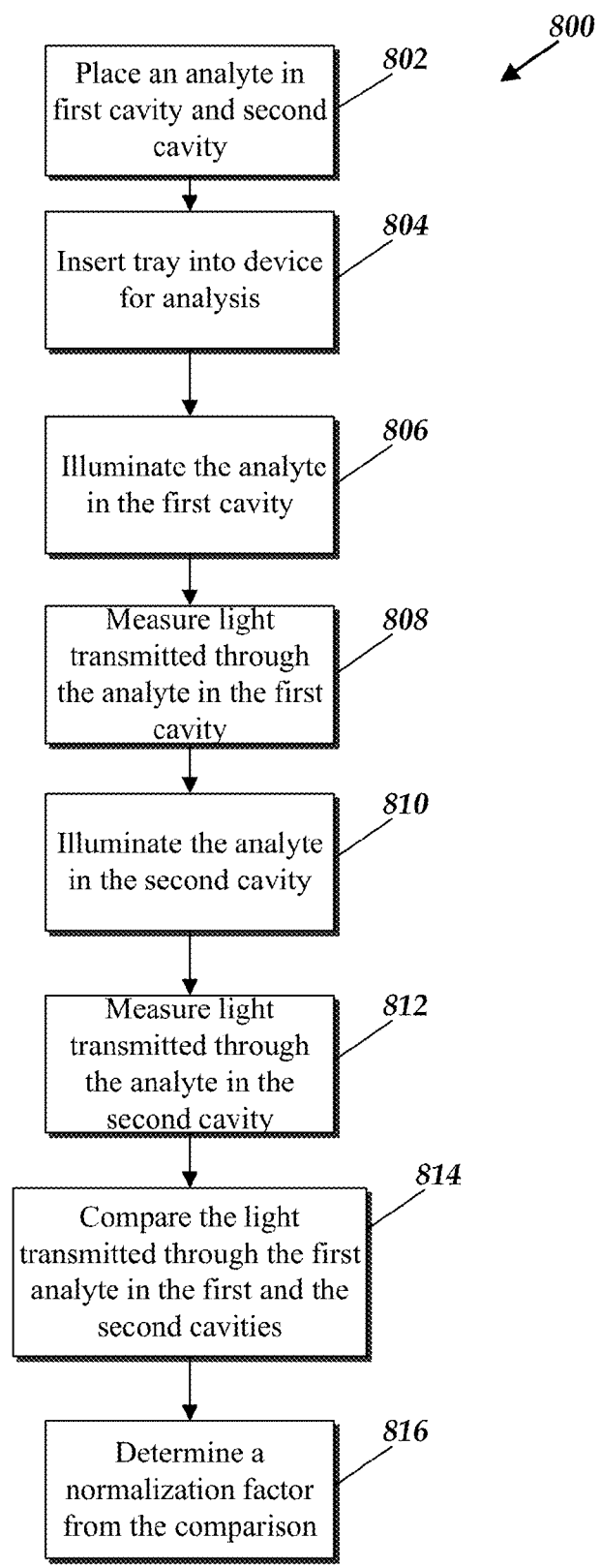

FIGS. 7A-E are views of an embodiment of a tray for measuring the concentration of a compound in a solvent according to the present disclosure; and FIG. 8 is a diagram of a method for measuring the concentration of a compound in a solvent according to the present disclosure.

DETAILED DESCRIPTION

Cannabis may be consumed in infusions or solutions in which the cannabis plant is mixed in a solvent and then pressed and filtered to express the plant compounds into the solvent using the lipophilic properties of the cannabis plant. For example, an infusion of tetrahydrocannabinol (THC) may be accomplished by boiling cannabis plant in water with butter, soaking the cannabis plant in oil, alcohol, and the like. Examples of solvents include cocoa butter, dairy butter, cooking oil, glycerin, skin lotions, and the like. Depending on the solvent, infusions may be used in the preparation of cannabis edibles like cakes, cookies, brownies, or other cooked or baked items. It is desirable to be able to quantify the concentration of THC, cannabinoids, terpenoids, and other therapeutic compounds in the infusion so that an appropriate amount of THC can be added during cooking or baking cannabis edibles. Quantifying the concentration of THC in infusions may be accomplished using gas chromatography or mass spectrometry, both of which are expensive and time consuming.

The present disclosure describes a system and method for determining the concentration of THC in an infusion that is inexpensive, quick, and generally accessible outside of a lab environment. An embodiment of the inventive system and method utilizes the high ultraviolet light absorption properties of THC for various wavelengths of light, e.g., ultraviolet (UV) light, to determine the concentration of THC in an analyte. In one embodiment, the system evaluates a first analyte comprising an infusion of a solvent and THC and a second analyte comprising the solvent only by illuminating both with a light emitting element and measuring the intensity of the transmitted light through each using a light receiving element to quantify relative concentrations of THC. The system may make parallel or sequential measurements of both the first and second analytes to improve accuracy. A control circuit quantifies the signal from each, performs the necessary calculations, and displays the result to the user.

Figure 1:
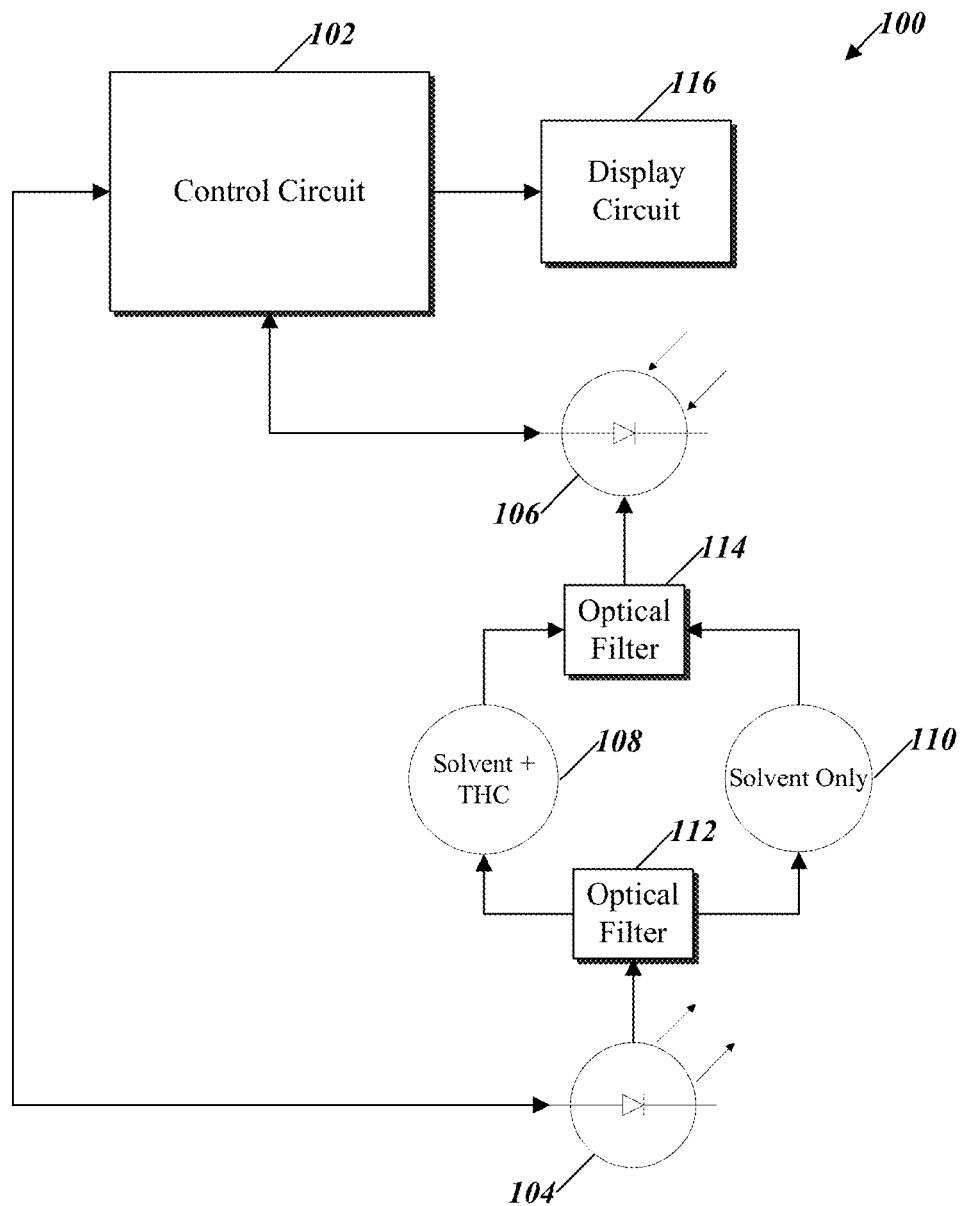

FIG. 1 is a block diagram of an embodiment of a system 100 for measuring the concentration of THC in an infusion according to the present disclosure. Referring to FIG. 1, system 100 comprises a control circuit 102 to control a light emitting element 104 and a light receiving element 106. Control circuit 102 may provide power to the light emitting element 104 and the light receiving element 106 by any means known to a person of ordinary skill in the art, including through the use of batteries. Control circuit 102 may cause light emitting element 104 to emit light of any wavelength, e.g., ultraviolet light. Light emitting element 104 may illuminate a first analyte 108 or a second analyte 110 either substantially simultaneously or sequentially. Light receiving element 106 may convert light transmitted through first analyte 108 or through second analyte 110 into an electronic signal that it provides to control circuit 102.

Light emitting element 104 may be any type of device capable of generating a light known to a person of ordinary skill in the art. Light emitting element 104 may comprise one or more lamps, incandescent bulbs, fluorescent bulbs, solid state light sources, light emitting diodes, and the like. Light emitting element 104 may include one or more light emitting diodes tuned to emit any wavelength of light including ultraviolet light, visible light, near-infrared light, and the like. Similarly, light receiving element 106 may be any type of device capable of receiving light known to a person of ordinary skill in the art. Light receiving element 106 may include one or more photodiodes tuned to receive or sense any wavelength of light including ultraviolet light, visible light, near-infrared light, and the like emitted from light emitting element 104. Light emitting diodes and photodiodes may be advantageously used in system 100 as light emitting element 104 and light receiving element 106, respectively, because they are low in cost and power consumption and high in reliability and space efficiency.

Light emitting element 104 or light receiving element 106 may be a single element or multiple elements depending on the particular implementation of system 100. Light emitting element 104 may be a single light emitting diode, a cluster of single light emitting diodes, or multiple light emitting dies within a single semiconductor package. Similarly, light receiving element 106 may be a single photodiode, a cluster of single photodiodes, or multiple photodiodes within a single semiconductor package. Multiple light emitting diodes may yield more optical power and improve reliability at the expense of power consumption and cost increases. Multiple photodiodes may improve sensitivity and reliability at the expense of cost increases. The general operation of light emitting element 104 and light receiving element 106 is well known to a person of ordinary skill in the art and will not be discussed further in any detail.

In an embodiment, light emitted from light emitting element 104 may be filtered before striking first analyte 108 or second analyte 110 using an optional optical filter 112 of any type. Similarly, light transmitted through first analyte 108 or second analyte 110 may be filtered using an optional optical filter 114 of any type.

Light emitting element 104 may be tuned to emit light of different wavelengths. Similarly, light receiving element 106 may be tuned to sense light of different wavelengths. By doing so, light emitting element 104 and light receiving element 106 may be able to extract additional information about first analyte 108 or second analyte 110 beyond a relative measure of THC concentration as we explain in more detail below.

Light emitting element 104 may be tuned to emit light of different intensities. By doing so, light emitting element 104 and light receiving element 106 may be able to extract a larger ranger of concentrations of the compounds in first analyte 108 and second analyte 110.

Figure 2A:
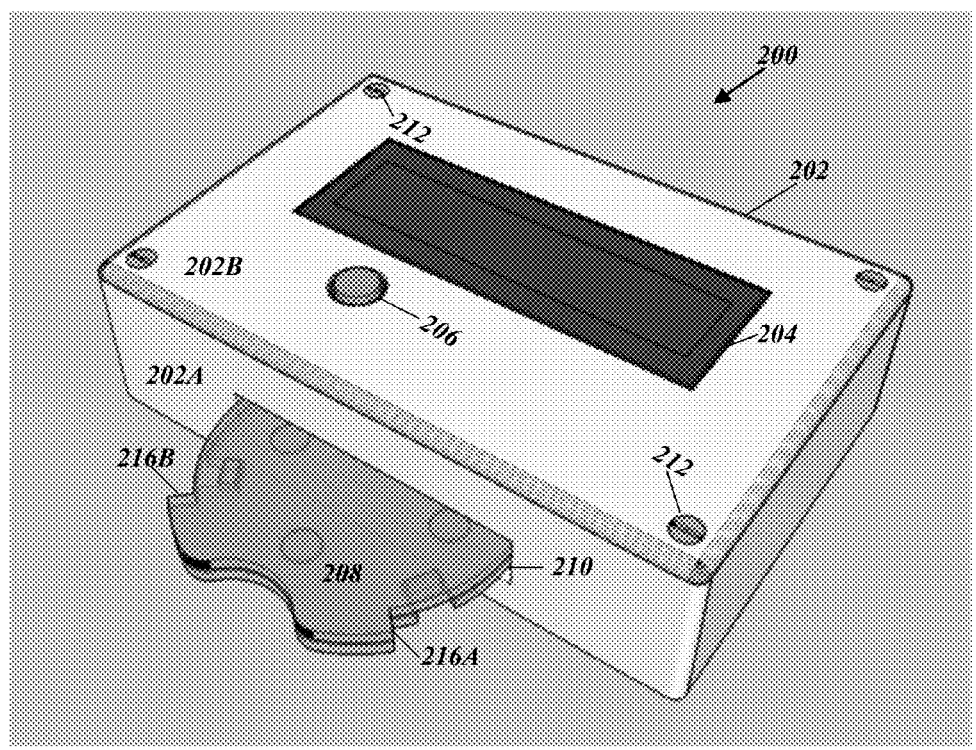

Control circuit 102 may further control display circuit 116 that, in turn, visually displays a concentration of THC to a user using display 204 shown in FIG. 2A.

Figure 2B:
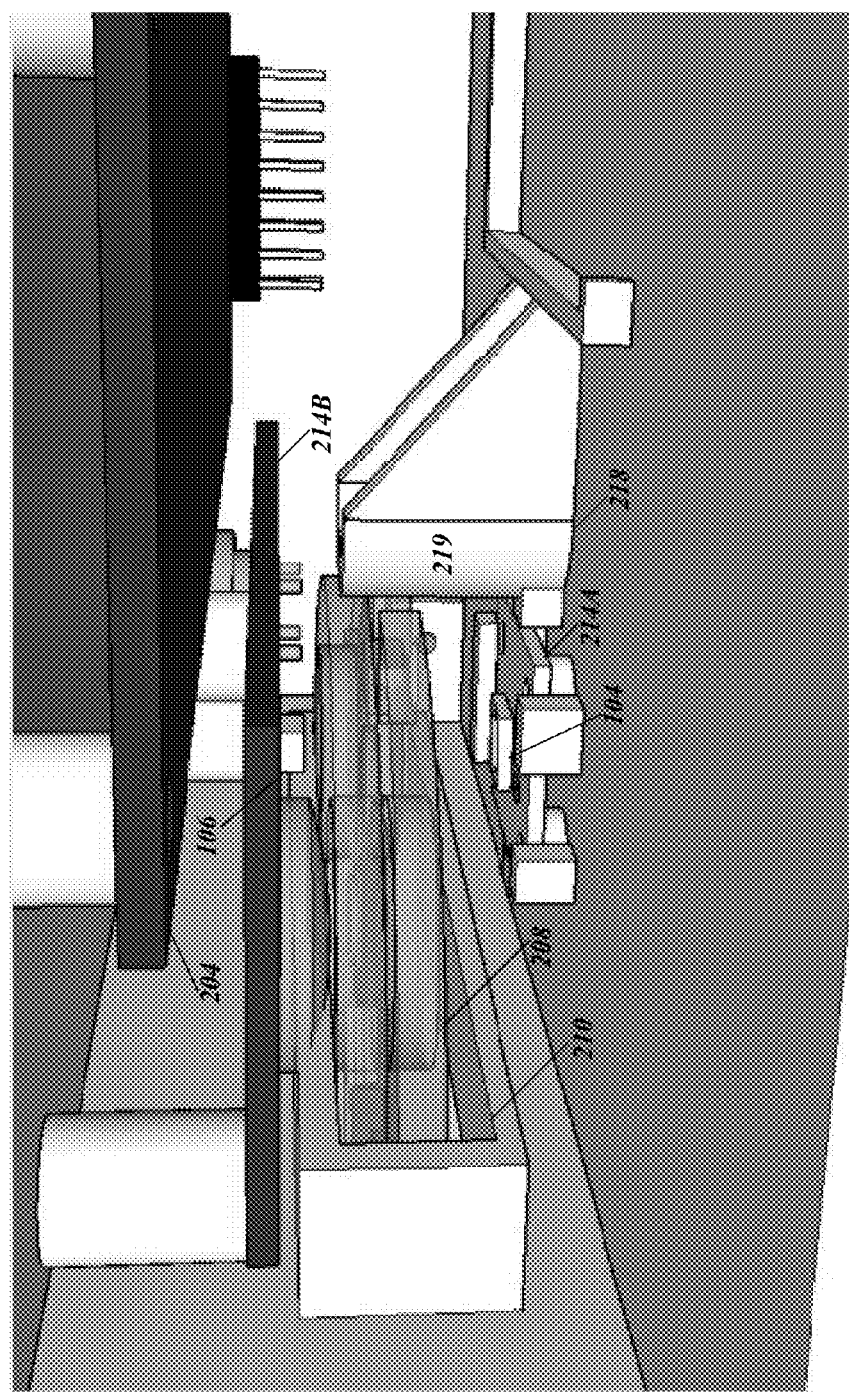
Figure 2C:
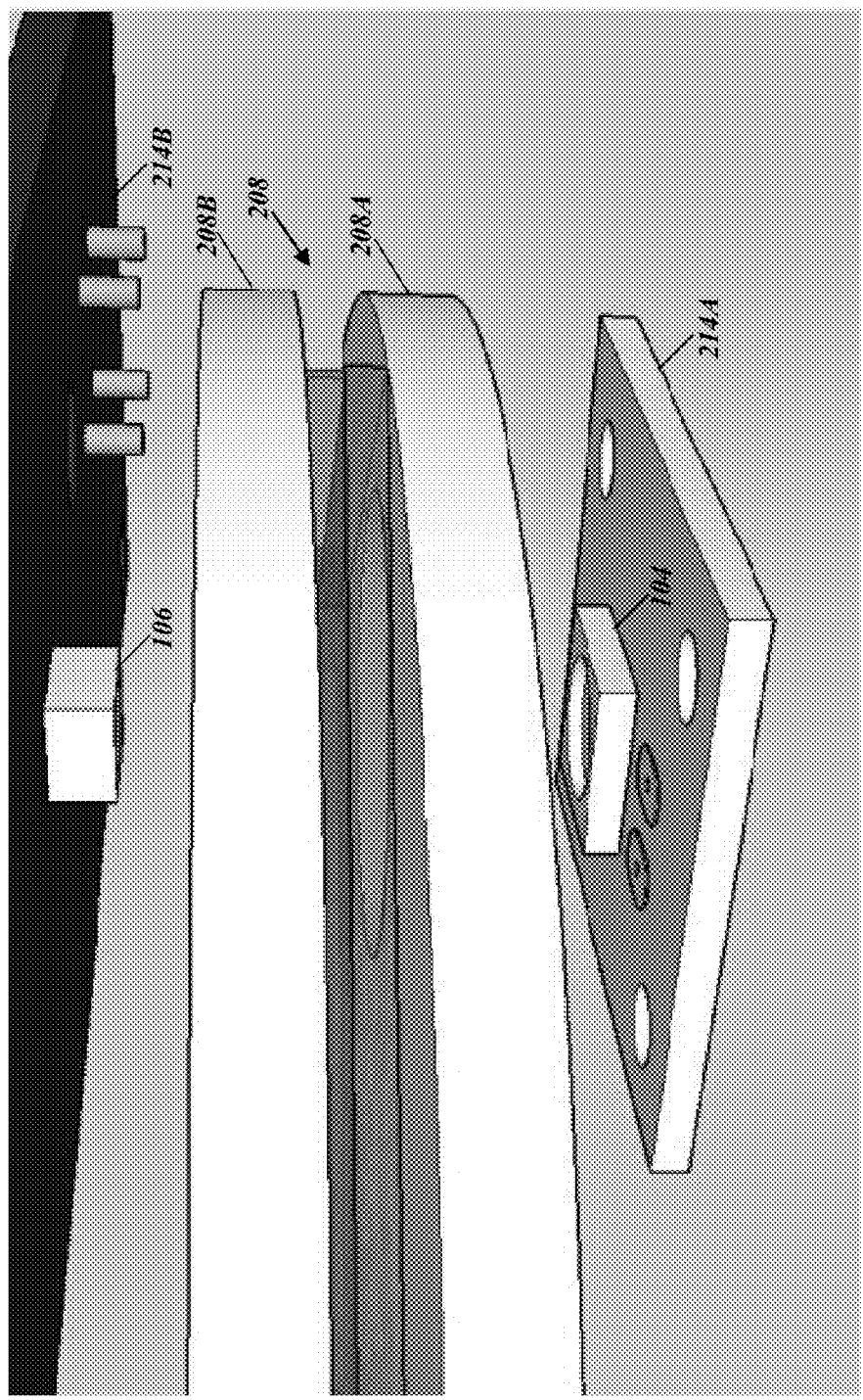

FIGS. 2A-C are different views of an embodiment of a device 200 for measuring the concentration of THC in an infusion according to the present disclosure. Referring to FIGS. 1 and 2A-C, device 200 comprises a housing 202 to house control circuit 102, display circuit 116, display 204, light emitting element 104, light receiving element 106, and optical filters 112 and 114. Housing 202 may receive a tray 208, in turn, containing first analyte 108 and second analyte 110, through a slot 210. Slot 210 may provide mechanical support for tray 208 and may aid in guiding tray 208 into position between light emitting element 104 and light receiving element 106 to facilitate analysis of first analyte 108 or second analyte 110. Alignment post 218 may provide a stop for insertion of tray 208 into housing 202.

Housing 202 may include a switch 206 to power device 200 on or off or to actuate certain menu options displayed on display 204. Switch 206 may operate under the control of circuit 102 and may be any type of switch, actuator, or button known to a person of ordinary skill in the art. Housing 202 may have any shape and size appropriate for its purpose including the rectangular shape shown in FIG. 2A. In an embodiment, housing 202 is sized to be hand-held and easily movable from one location to another. Housing 202 may be made of any material appropriate for its purpose including plastic materials of any type known to a person of ordinary skill in the art. Housing 202 may comprise a bottom portion 202A and a top portion 202B secured together using any type of fasteners 212, e.g., screws, snaps, and the like.

As shown best in FIGS. 2B-C, housing 202 may house control circuit 102 comprising printed circuit assemblies 214A and 214B that may mechanically support and electrically connect the electronic components of control circuit 102 using conductive tracks, pads, and other features etched from copper sheets laminated onto a non-conductive substrate. Printed circuit assemblies 214A and 214B may be single or double sided or multi-layered printed circuit boards. Conductors on different layers may be connected with plated-through holes called vias. Printed circuit assemblies 214A and 214B may include components, e.g., capacitors, resistors, or active devices, that are mounted using through holes or soldered directly onto a surface of printed circuit assemblies 214A or 214B.

Housing 202 may house display circuit 116 and display 204 to provide a user a visual interface to control operation of the device 100 and to display the results of the analysis of first analyte 108 and second analyte 110. Display 204 may be any kind of display, digital or otherwise, segment or two-dimensional, known to a person of ordinary skill in the art.

Figure 6:
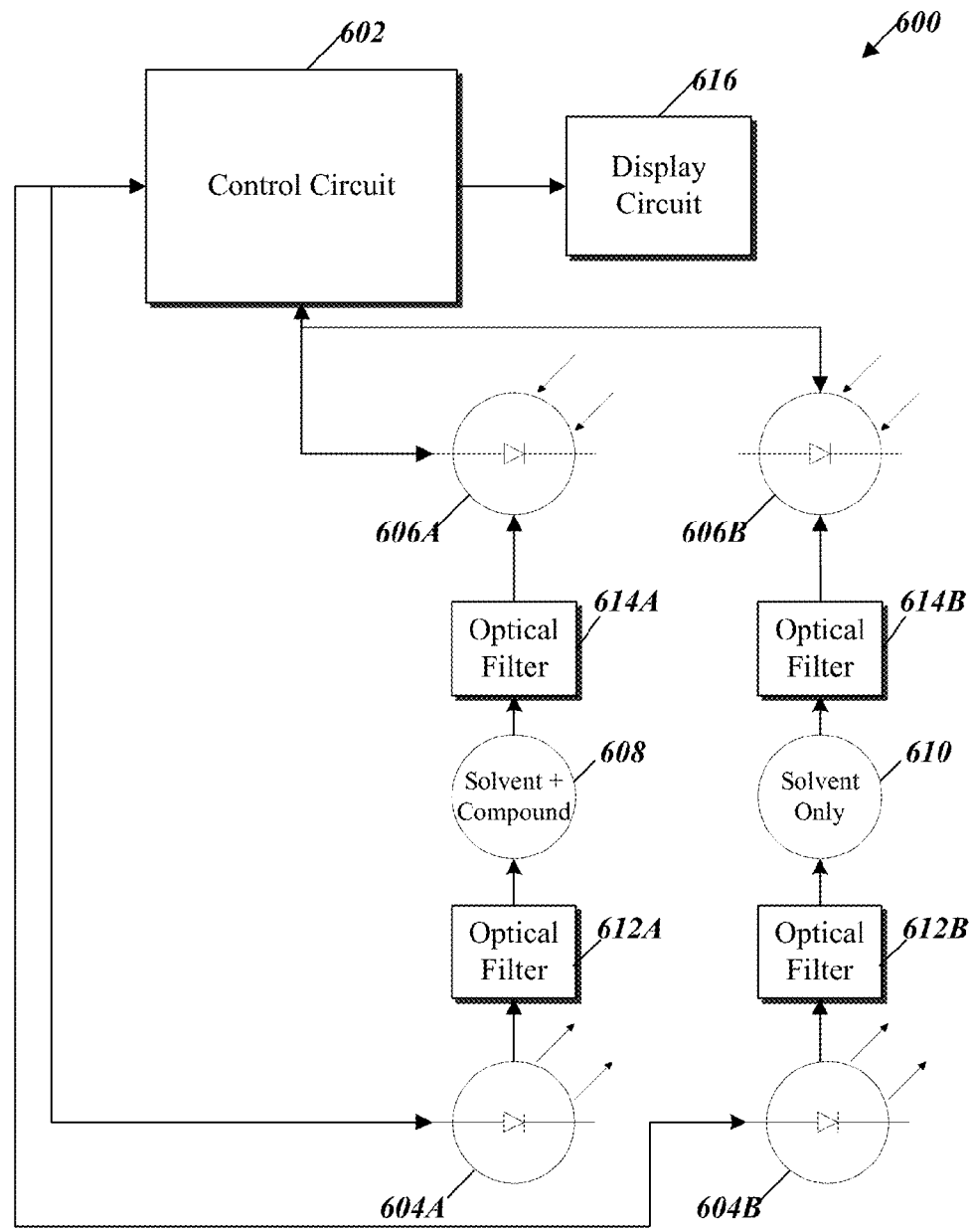
FIG. 6 is a block diagram of an embodiment of a system for measuring the concentration of compound in a solvent according to the present disclosure.

Housing 202 may house light emitting element 104 vertically optically aligned with light receiving element 106 on either side of tray 208. Light emitting element 104 may be mounted to a printed circuit assembly 214A while light receiving element 106 may be mounted to a printed circuit assembly 214B. Printed circuit assembly 214A may be coupled to printed circuit assembly 214B to allow control circuit 102 to control operation of light emitting element 104 and light receiving element 106. Printed circuit assemblies 214A and 214B may include printed circuit boards made of any material known to a person of ordinary skill in the art. Light emitting element 104 and light receiving element 106 are positioned within housing 202 such that light generated by light emitting element 104 propagates or transmits through first analyte 108 or second analyte 110 on tray 208 to light receiving element 106. In some embodiments, system 200 may include a dedicated pair including a light emitting element 104 and a light receiving element 106 for each analyte as shown in FIG. 6. Where a tray 200 or a tray 700 includes two different analytes 108 and 110 contained in distinct cavities, system 200 may include two distinct optical paths each, in turn, including a light emitting element 104 and a light receiving element 106 pair also as shown in FIG. 6.

Housing 202 may house one or more batteries (not shown) of any type to provide power to control circuit 102, light emitting element 104, light receiving element 106, display circuit 116, or display 204.

Tray 208 may comprise a bottom section 208A and a top section 208B having a substantially circular outer circumference and may be configured to contain first analyte 108 and second analyte 110. Bottom section 208A may lock to top section 208B using any kind of known locking feature built into or distinct from bottom section 208A or top section 208B. Tray 208 may comprise any material or combination of suitable materials including plastics of any type.

Tray 208 may be received in slot 210 of apparatus 200 to present first analyte 108 or second analyte 110 for analysis. Alignment stop 218 may locate tray 208 in device 200 by preventing tray 208 from being inserted too far into device 200. Stop 218 may have a curved surface 219 to allow for counterclockwise rotation of tray 208 up to rotational end stop 216A or for clockwise rotation of tray 208 up to rotational end stop 216B.

Figure 3A:
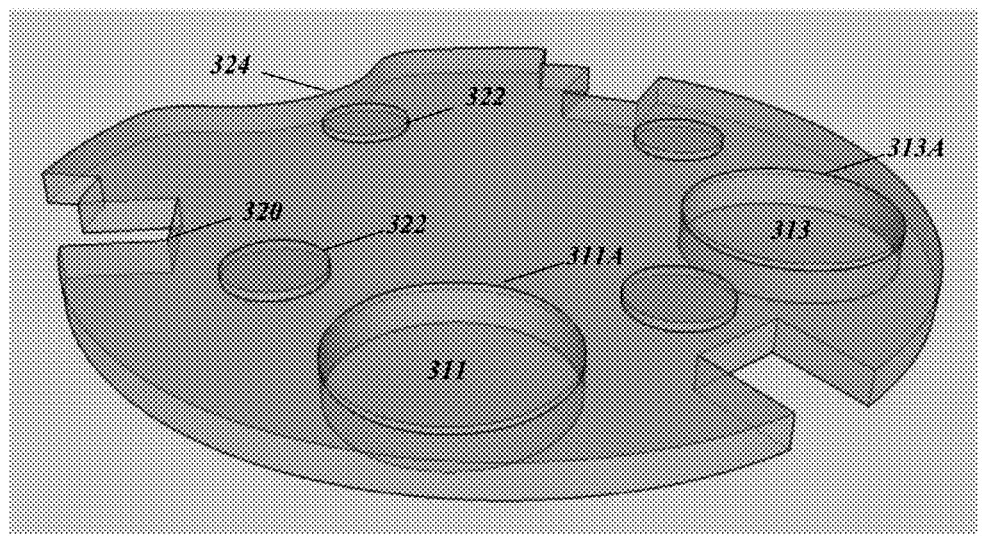
Figure 3B:
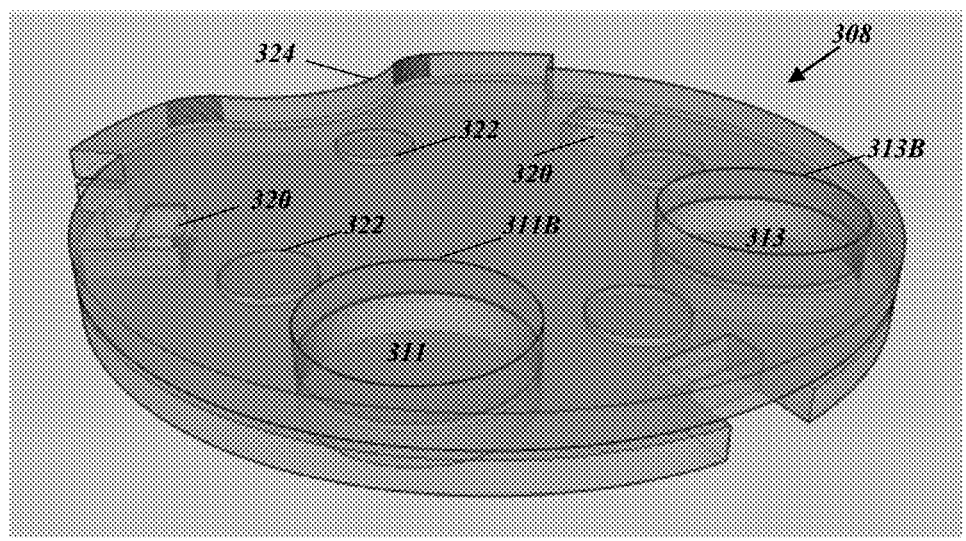
Figure 3C:
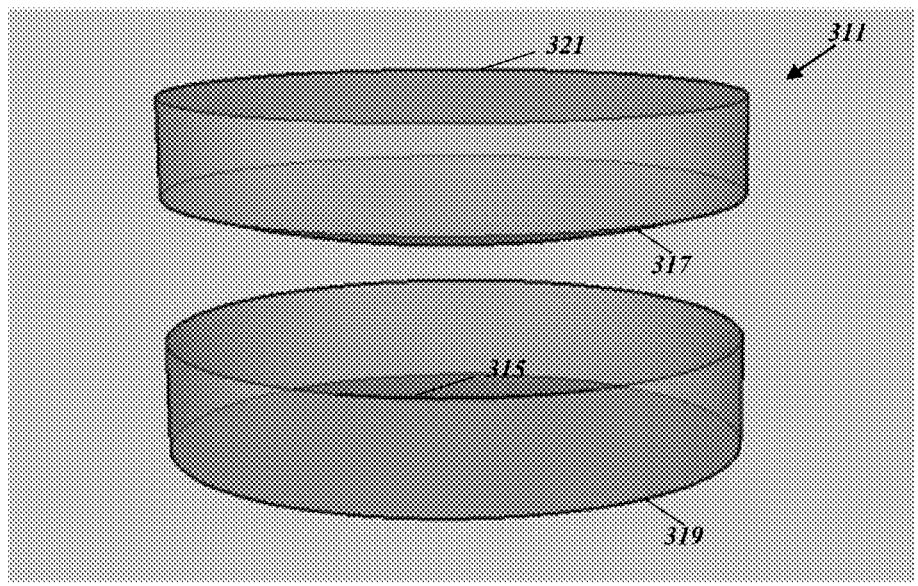

Tray 208 is shown in more detail as tray 308 in FIGS. 3A-C. Referring to FIGS. 2A-C and 3A-C, tray 308 comprises a bottom section and a top section that lock or snap together with locking features 320. Locking features 320 may be latches, snaps, or the like built into bottom section 308A that are received by notches or the like built into top section 308B. Alternatively, locking features 320 may be latches, snaps, or the like built into top section 308B that are received by notches or the like built into bottom section 308A. Locking features 320 may be fasteners distinct from bottom section 308A or top section 308B. Locking features 320 may comprise any material known to a person of ordinary skill in the art including plastics of any type. Locking features 320 may be self-releasing to ensure that bottom section 308A secures to top section 308B (or that top section 308B secures to bottom section 308A) without disturbing first analyte 108 or second analyte 110.

Tray 308 may comprise alignment features 322 built into bottom section 308A that are received by top section 308B that allow for alignment between bottom section 308A and top section 308B in the x, y, and z axis. Conversely, alignment features 322 may be built into top section 308B. Alignment features 322 may have a predetermined height so as to align top section 308A a known vertical distance from bottom section 308B to ensure that first analyte 108 or second analyte 110 has a uniform thickness across a first analyte cavity 311 or a second analyte cavity 313. Alignment features 322 are shown as having a cylindrical shape but other shapes come within the scope of the present disclosure.

Tray 308 may comprise a semicircular thumb well 324 to facilitate insertion of tray 308 into slot 210 of device 200. Thumb well 324 may facilitate clockwise and counterclockwise rotation of tray 308 about rounded surface 219 of post 218 to present first analyte 108 or second analyte 110 for analysis.

First analyte cavity 311 may comprise a first bottom cavity 311A and a first top cavity 311B. Similarly, second analyte cavity 313 may comprise a second bottom cavity 313A and a second top cavity 313B. First bottom cavity 311A and first top cavity 311B together may contain first analyte 108 (or second analyte 110) when bottom section 308A is secured to top section 308B using locking features 320. Similarly, second bottom cavity 313A and second top cavity 313B may contain second analyte 110 (or first analyte 108) when bottom section 308A is secured to top section 308B using locking features 320.

As best shown in FIG. 3C, first bottom cavity 311A may have a substantially concave surface 315 and first top cavity 311B may have a substantially convex surface 317. When bottom section 308A is secured to top section 308B of tray 308, the convex surface 317 of first top cavity 311B spreads first analyte 108 (or second analyte 110) about the concave surface 315 of first bottom cavity 311A to ensure that first analyte 108 has a uniform thickness throughout first cavity 311. Second bottom cavity 313A and second top cavity 313B may have a construction similar to that shown in FIG. 3C. Note that a height of the alignment features 322 may determine a size of a space between first bottom cavity 311A and first top cavity 311B (or between second bottom cavity 313A and second top cavity 313B) when bottom section 308A is secured to top section 308B to thereby set a thickness of first analyte 108 or second analyte 110 presented for analysis. The meniscus or bowl shape created in analyte cavities 311 and 313 may additionally aid in removal of bubbles within the first analyte 108 or second analyte 110 as the bottom section 308A is secured to the top section 308B. Analyte cavity 311 may be proud relative to immediately surrounding surfaces to allow excess analyte to overflow the edges of first cavity 311 without risk of contaminating an in second cavity 313. Similarly, analyte cavity 313 may be proud relative to immediately surrounding surfaces to allow excess analyte to overflow the edges of second cavity 313 without risk of contaminating an analyte in first cavity 311.

First analyte cavity 311 or second analyte cavity 313 may be made of any material known to a person of ordinary skill in the art including light transmissible (or optically clear) materials such as plastics. First cavity 311 or second cavity 313 may be made of any materials known to a person of ordinary skill in the art including optically clear materials such as plastics. As such, first cavity 311 or second cavity 313 may form part of an optical path between light emitting element 104 and light receiving element 106. First bottom cavity 311A, first top cavity 311B, second bottom cavity 313A, and second top cavity 313B may have a variety of other shapes depending on a variety of design characteristics of tray 308, including characteristics associated with the design of the optical path between light emitting element 104 and light receiving element 106. First bottom cavity 311A may have a concave surface 315 opposing a flat end (as shown in FIG. 3C), a convex end, or a concave end 319 while first top cavity 311B may have a convex surface 317 opposing a flat end (as shown in FIG. 3C), a convex end, or a concave end 321 depending on the performance characteristics of the optical path between light emitting element 104 and light receiving element 106.

First analyte cavity 311 or second analyte cavity 313 may be built into bottom section 308A or top section 308B or be distinct from bottom section 308A or top section 308B, e.g., by using separate glass slides and cover slips to contain first analyte 108 or second analyte 110.

Figure 4:
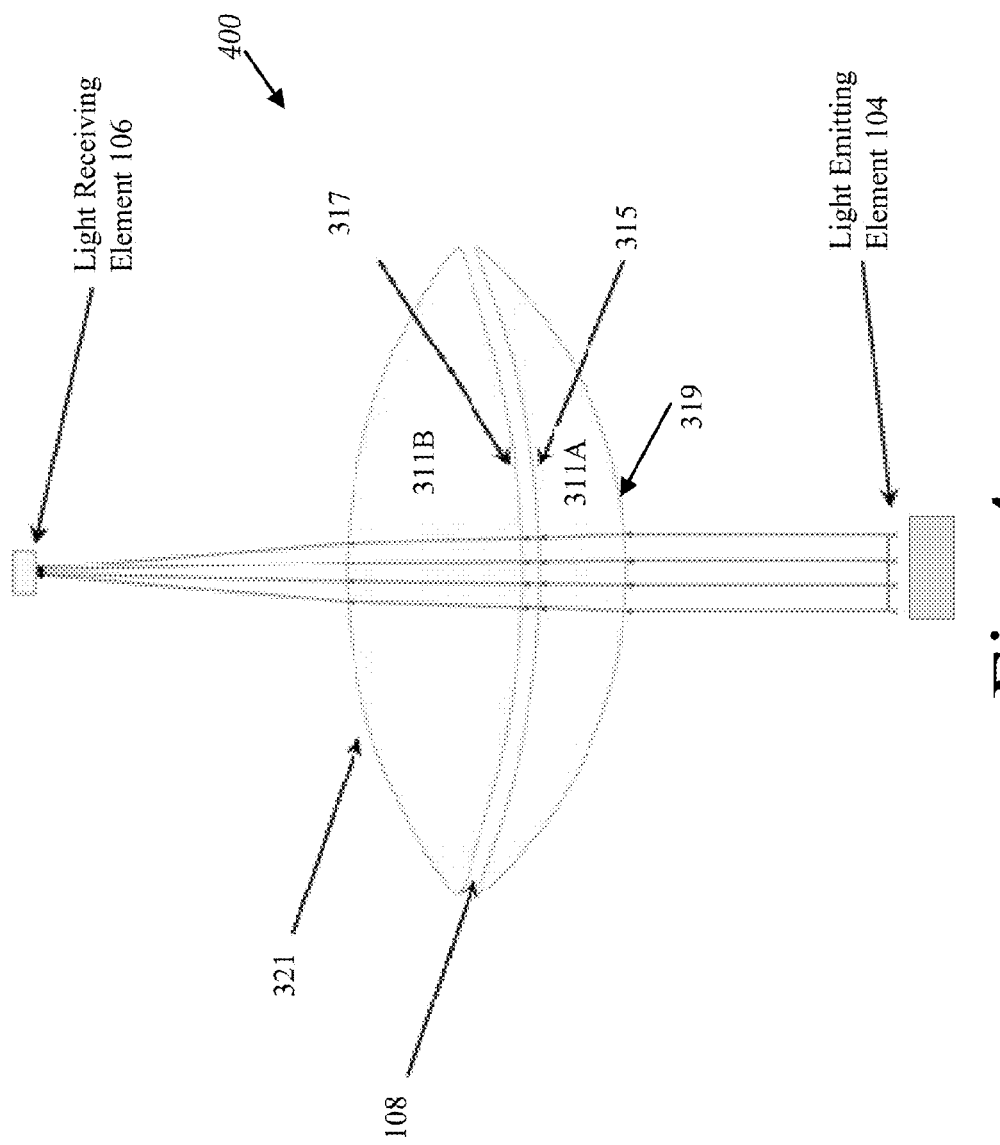
FIG. 4 is a diagram of an embodiment of an optical path for measuring the concentration of THC in an infusion according to the present disclosure.

FIG. 4 is a diagram of an optical path 400 between light emitting element 104 and light receiving element 106 through first analyte 108. Referring to FIGS. 1, 2A-C, 3A-C, and 4, once tray 308 is inserted into device 200, light emitting element 104 generates a light that illuminates cavity 311 containing first analyte 108. First bottom section 311A comprises concave surface 315 and first top section 311B comprises a convex surface 317 that spread analyte 108 uniformly over its length. A convex surface 319 opposes concave surface 315 on first bottom section 311A while convex surface 321 opposes convex surface 317 on bottom section 311B, all of which comprise optically clear materials that may filter the light from light emitting element 108. In an embodiment, the biconvex shape of optically-clear first bottom section 311A secured to first top section 311B may focus the light transmitted through first analyte 108 on to light receiving element 106. A person of ordinary skill in the art should recognize that bottom section 311A and top section 311B may be shaped to variously filter or focus the light emitted from light emitting element 104.

Figure 5:
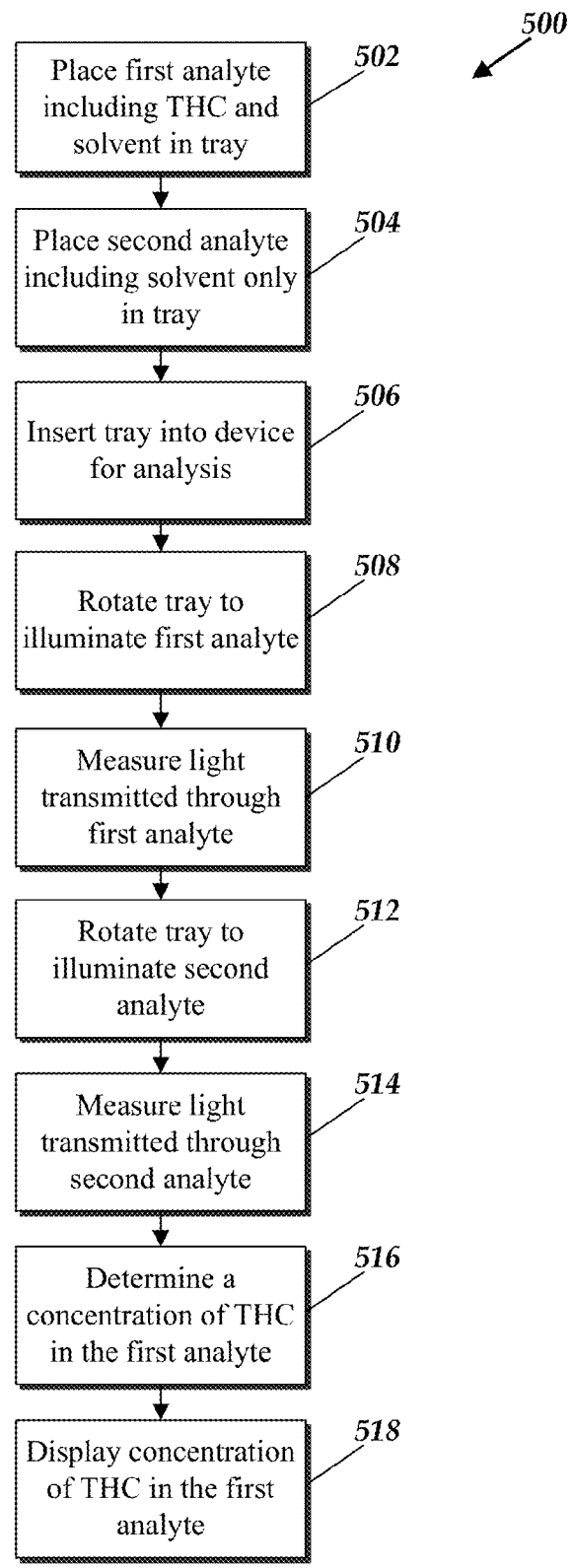
FIG. 5 is a diagram of a method for measuring the concentration of THC in an infusion according to the present disclosure.

FIG. 5 is a diagram of a method 500 for measuring the concentration of THC in a solvent according to the present disclosure. Referring to FIG. 5, at step 502, method 500 includes placing a first analyte including a solvent and THC in a first cavity of a tray and, at step 504, placing a second analyte including the solvent only in a second cavity of the tray. At step, 506, method 500 includes inserting the tray into the device for analysis. At step 508, method 500 includes rotating the tray such that the first analyte is placed in an optical path between a light emitting element and a light receiving element. At step 510, method 500 includes illuminating the first analyte using the light emitting element and measuring the light transmitted through the first analyte using the light receiving element. At step 512, method 500 includes rotating the tray such that the second analyte is placed in the optical path between the light emitting element and the light receiving element. At step 514, method 500 includes illuminating the second analyte using the light emitting element and measuring the light transmitted through the second analyte using the light receiving element. At step 516, method 500 includes determining a concentration of THC in the first analyte by comparing the light transmitted through the first analyte and the light transmitted through the second analyte. At step 518, method 500 includes displaying the concentration of THC. During steps 506, 508, 510, 512, and 514, a same light emitting element and light receiving elements may be used to detect the various positions of the tray.

FIG. 6 is a block diagram of an embodiment of a system 600 for measuring the concentration of a compound in a solvent according to the present disclosure. Referring to FIG. 6, system 600 comprises a control circuit 602 to control light emitting elements 604A and 604B and light receiving elements 606A and 606B. Control circuit 602 may provide power to light emitting elements 604A and 604B and light receiving elements 606A and 606B by any means known to a person of ordinary skill in the art, including through the use of batteries. Control circuit 602 may cause light emitting elements 604A and 604B to emit light of any wavelength, e.g., ultraviolet light. Light emitting elements 604A and 604B may illuminate a first analyte 608 or a second analyte 610 either substantially simultaneously or sequentially. Light receiving element 606A may convert light transmitted through first analyte 608 into an electronic signal that it provides to control circuit 602. Likewise, light receiving element 606B may convert light transmitted through second analyte 610 into an electronic signal that it provides to control circuit 602.

Light emitting elements 604A and 604B may be any type of device capable of generating a light known to a person of ordinary skill in the art. Light emitting elements 604A and 604B may comprise one or more lamps, incandescent bulbs, fluorescent bulbs, solid state light sources, light emitting diodes, and the like. Light emitting elements 604A and 604B may include one or more light emitting diodes tuned to emit any wavelength of light including ultraviolet light. Similarly, light receiving elements 606A and 606B may be any type of device capable of receiving light known to a person of ordinary skill in the art. Light receiving elements 606A and 606B may include one or more photodiodes tuned to receive or sense any wavelength of light including ultraviolet light emitted from light emitting elements 604A and 604B. Light emitting diodes and photodiodes may be advantageously used in system 600 as light emitting elements 604A and 604B and light receiving elements 606A and 606B, respectively, because they are low in cost and power consumption and high in reliability and space efficiency.

Light emitting elements 604A and 604B or light receiving elements 606A and 606B may be a single element or multiple elements depending on the particular implementation of system 600. Light emitting elements 604A and 604B may be a single light emitting diode, a cluster of single light emitting diodes, or multiple light emitting dies within a single semiconductor package. Similarly, light receiving elements 606A and 606B may be single photodiode, a cluster of single photodiodes, or multiple photodiodes within a single semiconductor package. Multiple light emitting diodes may yield more optical power and improve reliability at the expense of power consumption and cost increases. Multiple photodiodes may improve sensitivity and reliability at the expense of cost increases. The general operation of light emitting elements 604A and 604B and light receiving elements 606A and 606B is well known to a person of ordinary skill in the art and will not be discussed further in any detail.

In an embodiment, light emitted from light emitting element 604A may be filtered before striking first analyte 608 using an optional optical filter 612A of any type. Light emitted from light emitting element 604B may be filtered before striking second analyte 610 using an optional optical filter 612B of any type. Similarly, light transmitted through first analyte 608 or second analyte 610 may be filtered using optional optical filters 614A and 614B, respectively, of any type.

Light emitting elements 604A and 604B may be tuned to emit light of different wavelengths. Similarly, light receiving elements 606A and 606B may be tuned to sense light of different wavelengths. By doing so, light emitting elements 604A and 604B and light receiving elements 606A and 606B may be able to extract additional information about first analyte 608 or second analyte 610 beyond a relative measure of compound concentration as we explain in more detail below.

Control circuit 602 may further control display circuit 616 that, in turn, visually displays a concentration of a compound in first analyte 608 to a user using, e.g., display 204 shown in FIG. 2A.

FIGS. 7A-E are views of an embodiment of a tray 700 for measuring the concentration of a compound in a solvent according to the present disclosure. Referring to FIGS. 1, 6, and 7A-E, tray 700 includes a top portion 710 coupled to a bottom portion 720 using a coupling mechanism 730. Coupling mechanism 730 may fixedly or removably attach top portion 710 to bottom portion 720. Top portion 710 may fully or partially disengage from bottom portion 720 or top portion 710 to allow for analyte loading, cleaning, inspection, and the like.

Tray 700 may be assembled by coupling, locking, or snapping top portion 710 to bottom portion 720 using coupling mechanism 730. Coupling mechanism 730 may be any kind of mechanism that joins or connects two solid objects known to a person of ordinary skill in the art. Coupling mechanism 730 may use mechanical principles, e.g., a hinge or latch, or electrical principles, e.g., an electromagnetic coupling, to couple top portion 710 to bottom portion 720. In some embodiments, coupling mechanism 730 may be a hinge that includes a mechanical bearing, pin, snap, or pivot point to allow a limited angle of rotation between top portion 710 and bottom portion 720 as is explained in more detail below. In other embodiments, coupling mechanism may snap or lock top portion 710 to bottom portion 720. Coupling mechanism 730 may be based on a magnet formed between top portion 710 and bottom portion 720.

In an embodiment, coupling mechanism 730 may be located at a single common end of top portion 710 and bottom portion 720 such that top portion 710 swings about a limited angle relative to bottom portion 720.

Coupling mechanism 730 may be fully or partially formed or assembled on top portion 710, bottom portion 720, or both top portion 710 and bottom portion 720. In an embodiment, coupling mechanism 730 may comprise a plurality of knuckles or flanges 718 formed on top portion 710 and a plurality of knuckles or flanges 728 formed on bottom portion 720. The plurality of knuckles or flanges 718 may mate or otherwise be received within the plurality of knuckles or flanges 728. Top portion 710 and bottom portion 720 may be made of any material known to a person of ordinary skill in the art, e.g., plastic, metal, or the like. Top portion 710 or bottom portion 720 may be cast or molded as a single part or cast or molded and assembled from various parts made of different or distinct materials.

In an embodiment, top portion 710 and bottom portion 720 may include snap or locking features 715 or 727 that allow top portion 710 to removably attach to bottom portion 720 alone or in combination with the plurality of knuckles or flanges 718 and 728. Locking feature 715 may mate, lock, snap, or otherwise coupled to locking feature 727. In an embodiment, locking feature 715 may be a protrusion, hollow or otherwise, having any shape known to a person of ordinary skill in the art. Locking feature 715 may extend or protrude outwardly from a face 714 of top portion 710. Locking feature 715 may be received by a cavity 727 formed on a face 729 of bottom portion 720. Locking feature 715 may include facets 715A along a top edge that temporarily give or compress to allow their insertion into cavity 727 while expanding after insertion to lock top portion 710 into bottom portion 720. In an embodiment, locking features 715 and 727 may be self-releasing to ensure that top portion 710 removably attaches to bottom portion 720. Locking features 715 and 727 may further align top portion 710 to bottom portion 720 in the x, y, and z axis. Locking feature 715 may be built into top portion 710 as shown in FIGS. 7A-E but may alternatively be built into or assembled as part of bottom portion 720. Similarly, locking feature 727 may be built into bottom portion 720 as shown in FIGS. 7A-E but may alternatively be built into or assembled as part of bottom portion 720.

Locking features 715 and 727 may have a predetermined vertical height so as to align top portion 710 a known or predetermined vertical distance from bottom portion 720 (similar to alignment features 322 shown in FIGS. 3A-C) to ensure that first analyte 108 or second analyte 110 has a uniform thickness 650 across first concave feature 721 or second concave feature 722. Locking features 715 and 727 may have any shape, e.g., cylindrical, and be made of any material, e.g., plastic, known to a person of ordinary skill in the art.

Top portion 710 may include a first convex feature 711 or a second convex feature 712 or both first concave feature 711 and second concave feature 712. First convex feature 711 or second convex feature 712 may have a substantially convex surface extending outward from top portion 710. First convex feature 711 or second convex feature 712 may have a substantially spherical or aspherical shape but other surface types and shapes come within the scope of the present disclosure.

Bottom portion 720 may include a first concave feature 721 to form first cavity 731 that contains a first analyte 608. First analyte 608 may comprise a compound, e.g., tetrahydrocannabinol, and a solvent, e.g., oil, liquid, and the like. Bottom portion 720 may likewise include a second concave feature 722 to form a second cavity 732 that contains a second analyte 610. Second analyte 610 may only comprise the solvent, e.g., oil, liquid, and the like. First concave feature 721 or second concave feature 722 may have substantially concave surfaces and may have substantially spherical or aspherical shapes but other surface types and shapes come within the scope of the present disclosure.

When tray 700 is assembled as shown in FIG. 7A, first concave feature 721 may mate or otherwise receive first convex feature 711 to form first cavity 731 contain first analyte 108 or 608. Similarly, when tray 700 is assembled, second concave feature 722 may mate or otherwise receive second convex feature 712 to form second cavity 732 contain second analyte 110 or 610.

When bottom portion 720 is secured to top portion 710 of tray 700 using, e.g., locking features 715 and 727, the first convex feature 711 may spread first analyte 108 or 608 (or second analyte 110 or 610) about the first concave feature 721 to ensure that first analyte 108 or 608 has a uniform thickness 750 throughout first concave feature 721. Note that a height of locking features 715, 727, or the alignment features 322 (FIGS. 3A and 3B), may determine a size of a space between first convex feature 711 and first concave feature 721 (or between second convex feature 712 and second concave feature 722) when bottom portion 720 is secured to top portion 710 to thereby ensure that a known predetermined thickness 750 of first analyte 108 or 608 or second analyte 110 or 610 is presented for analysis. The meniscus or bowl shape created in first concave feature 721 or second concave feature 722 may additionally aid in removal of bubbles within the first analyte 108 or 608 or second analyte 110 or 610.

First concave feature 721 may be proud relative to immediately surrounding surfaces to allow excess analyte to overflow the edges of first concave feature 721 into well 723 without risk of contaminating second analyte 110 in second concave feature 722. Similarly, second concave feature 722 may be proud relative to immediately surrounding surfaces to allow excess analyte to overflow the edges of second concave feature 722 into well 723 without risk of contaminating first analyte 108 in first concave feature 721. Well 723 may surround first concave feature 721 and second concave feature 722. A rim 713 may protrude from top portion 710 such that when tray 700 is assembled, rim 713 is received within well 723 to contain any excess analyte. An absorbent liner (not shown separately from tray 700) may fit within well 723 to soak up any excess analyte. The liner may be disposable and made of any absorbent material known to a person of ordinary skill in the art, e.g., sponge, paper, cloth, or the like.

Similar to first cavity 311 or second cavity 313 shown in FIGS. 3A and 3B, first concave feature 721, second concave feature 722, first convex feature 711, and second convex feature 712 may be made of any materials known to a person of ordinary skill in the art including optically clear materials such as plastics. First concave feature 721, second concave feature 722, first convex feature 711, and second convex feature 712 may form part of an optical path between light emitting element 104 and light receiving element 106.

A gap formed between first concave feature 721 and first convex feature 711 and second concave feature 722 and second convex feature 712 when tray 700 is assembled, may vary with manufacturing processes. Before first use, therefore, system 100 or 200 may calibrate tray 700 to account for these manufacturing variances. FIG. 8 is a diagram of a method for calibrating a tray 700 according to the present disclosure. Referring to FIGS. 1, 6, 7A-E, and 8, at step 802, method 800 includes placing a same analyte in both a first cavity and a second cavity for purposes of calibrating tray 700. At step 804, method 800 includes inserting tray 700 into system 100 or 600 for analysis. At 806, method 800 illuminates the analyte in the first cavity and, at step 808, method 800 measures the light transmitted through the analyte in the first cavity. At 810, method 800 illuminates the analyte in the second cavity and, at step 812, method 800 measures the light transmitted through the analyte in the second cavity. At step 814, method 800 compares the light transmitted through the analyte in both the first and second cavities to determine a cavity normalization factor at step 816.

In some circumstances, a luminous intensity of each light emitting element 604A and 604B may vary with ambient temperature. Furthermore, the temperature of the light emitting elements 604A and 604B may change with use, resulting in changes to luminous intensity. In an embodiment, these effects may be stabilized by repeatedly turning the light emitting elements 604A and 604B on and off, and measuring the light received by light receiving elements 606A and 606B until a certain predetermined threshold luminosity has been reached or until reaching a predetermined range of luminosity indicative of stabilization of light emitting elements 604A and 604B that result in the calculation of a light emitting element normalization factor for each light emitting element 604A and 604B.

In an embodiment, systems 100 or 600 may determine the concentration of a compound in the first analyte as follows:

(light transmitted through the first analyte+first cavity normalization factor+first cavity light emitting element normalization factor)−(light transmitted through the second analyte+second cavity normalization factor+second cavity light emitting diode normalization factor) =compound absorptivity Where:

first cavity normalization factor may refer to a normalization factor obtained prior to testing the compound by measuring the light transmitted through the same solvent placed in both the first and second cavities;

first cavity light emitting diode normalization factor may refer to a normalization factor obtained by testing the light emitting diodes prior to inserting the analyte tray in the system;

second cavity normalization factor may refer to a normalization factor obtained prior to testing the compound by measuring the light transmitted through the same solvent placed in both the first and second cavities; and second cavity light emitting diode normalization factor may refer to a normalization factor obtained by testing the light emitting diodes prior to inserting the analyte tray in the system.

In some embodiments, the resulting compound absorptivity may be used in conjunction with a lookup table or mathematical equation to calculate the concentration of the dissolved compound. This mathematical equation may be exponential, logarithmic, linear, quadratic, polynomial, or the like. The mathematical function or lookup table for calculating compound density may be different for each class of solvents.

Normalization factors may be positive or negative numbers depending on the specific implementation of system 100. Compound absorptivity may be an absolute value (always>0) for the purpose of calculating compound density.

In circumstances where compounds are phytocannabinoids, the compound density may be expressed as a Cannabinoid By Volume (CBV) number with the units mg/ml or milligrams of cannabinoids per milliliter of solvent.

The present disclosure includes examples of one or more embodiments. It is, of course, not possible to describe every conceivable modification and alteration of the above systems or methodologies for purposes of describing the aforementioned aspects, but one of ordinary skill in the art can recognize that many further modifications and permutations of various aspects are possible. Accordingly, the present disclosure describes aspects intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

A person of ordinary skill in the art will appreciate that the present disclosure is not limited to what has been particularly shown and described hereinabove. Rather, the scope of the present disclosure includes both combinations and subcombinations of the various features described hereinabove as well as modifications and variations which would occur to such skilled persons upon reading the foregoing description. Thus the disclosure is limited only by the appended claims.

The invention claimed is:

1. An apparatus, comprising:
a tray including:
    a bottom including a first concave portion to contain a first analyte having a compound and a solvent and a second concave portion to contain a second analyte having the solvent;
    a top including a first convex portion and a second convex portion;
    a coupling mechanism to removably attach the top to the bottom to thereby mate the first convex portion to the first concave portion distributing the first analyte substantially evenly across the first concave portion and to mate and the second convex portion to the second concave portion distributing the second analyte substantially evenly across the second concave portion;
a light emitting device configured to generate a light to illuminate the first analyte and the second analyte contained in the tray;
a light receiving device configured to receive a first portion of the light transmitted through the first analyte and configured to receive a second portion of the light transmitted through the second analyte; and
a control circuit configured to determine a concentration of the compound in the first analyte based at least in part on a comparison of the first portion of the light transmitted through the first analyte and the second portion of the light transmitted through the second analyte.

2. The apparatus of claim 1,
wherein the first analyte includes a first compound and a first solvent; and
wherein the second analyte includes the first solvent.

3. The apparatus of claim 1,
wherein the coupling mechanism removably attaches the bottom portion to the top portion maintaining the first analyte or the second analyte at a predetermined substantially even thickness across the first concave feature or the second concave feature, respectively.

4. The apparatus of claim 1,
wherein the bottom portion further includes a well surrounding the first concave feature and the second concave feature;
wherein the top portion further includes a rim surrounding the first convex feature and the second convex feature; and
wherein the rim is received within the well when the coupling mechanism removably attaches the bottom portion to the top portion to define a capture area that contains an excess of the first analyte or the second analyte.

5. The apparatus of claim 4, further comprising:
a disposable absorbent liner positioned within the well to absorb the excess of the first analyte or the second analyte.

6. The tray apparatus of claim 1,
wherein the first concave feature or the second concave feature is spherical or aspherical.

7. The tray apparatus of claim 1,
wherein the first convex feature or the second convex feature is spherical or aspherical.

8. The apparatus of claim 1, further comprising:
at least one alignment feature to align the first concave feature to the first convex feature or to align the second concave feature to the second convex feature.

9. The apparatus of claim 1, further comprising:
at least one alignment feature to uniformly vertically space the top from the bottom.

10. The apparatus of claim 1,
wherein the light emitting device is further configured to illuminate the second analyte in the second concave feature;
wherein the light receiving device is further configured to receive the second portion of the light transmitted through the second analyte; and
wherein the control circuit is further configured to calculate the concentration of the compound in the first analyte based at least in part on the first portion of the light and the second portions of the light.

11. The apparatus of claim 1, further comprising:
a locking feature to lock the top to the bottom.

12. The apparatus of claim 1, further comprising a display to display the concentration of the compound in the first analyte.

13. A method, comprising:
containing a first analyte having a compound and a solvent in a first concave portion of a bottom of a tray;
containing a second analyte having the solvent in a second concave portion of the bottom of the tray;
including a first convex portion and a second convex portion in a top of the tray;
removably mating the first convex portion to the first concave portion distributing the first analyte substantially evenly across the first concave portion and removably mating the second convex portion to the second concave portion distributing the second analyte substantially evenly across the second concave portion;
generating a light to illuminate the first analyte and the second analyte contained in the tray;
receiving a first portion of the light transmitted through the first analyte;
receiving a second portion of the light transmitted through the second analyte; and
determining a concentration of the compound in the first analyte based at least in part on a comparison of the first portion of the light transmitted through the first analyte and the second portion of the light transmitted through the second analyte.

* * * * *